United States Patent [19]

Mann

[11] Patent Number: 5,287,857

[45] Date of Patent: Feb. 22, 1994

[54] APPARATUS AND METHOD FOR OBTAINING AN ARTERIAL BIOPSY

[76] Inventor: David Mann, 4720 Everts St., San Diego, Calif. 92109

[21] Appl. No.: 901,830

[22] Filed: Jun. 22, 1992

[51] Int. Cl.$^5$ .............................................. A61B 10/00
[52] U.S. Cl. .................................................... 128/753
[58] Field of Search ................................ 128/751-754; 606/167, 170

[56] References Cited

U.S. PATENT DOCUMENTS

| | | | |
|---|---|---|---|
| 3,606,878 | 9/1971 | Kellogg, Jr. | 128/2 B |
| 3,732,858 | 5/1973 | Banko | 128/753 |
| 3,830,225 | 8/1974 | Shinnick | 128/2 B |
| 3,929,126 | 12/1975 | Corsaut | 128/240 |
| 4,099,518 | 7/1978 | Baylis et al. | 128/2 B |
| 4,249,541 | 2/1981 | Pratt | 128/753 |
| 4,396,021 | 8/1983 | Baumgartner | 128/753 |
| 4,411,055 | 10/1983 | Simpson et al. | 29/447 |
| 4,465,072 | 8/1984 | Taheri | 128/348.1 |
| 4,617,940 | 10/1986 | Wang | 128/753 |
| 4,619,263 | 10/1986 | Frisbie et al. | 128/344 |
| 4,620,547 | 11/1986 | Boebel | 128/754 |
| 4,640,296 | 2/1987 | Schnepp-Pesch et al. | 128/754 |
| 4,641,654 | 2/1987 | Samson et al. | 128/344 |
| 4,681,123 | 7/1987 | Valtchev | 128/753 |
| 4,692,200 | 9/1987 | Powell | 156/289 |
| 4,693,257 | 8/1987 | Markham | 128/752 |
| 4,708,147 | 12/1987 | Haaga | 128/753 |
| 4,723,936 | 2/1988 | Buchbinder et al. | 604/95 |
| 4,762,130 | 8/1988 | Fogarty et al. | 128/348 |
| 4,763,667 | 8/1988 | Manzo | 128/750 |
| 4,763,668 | 8/1988 | Macek et al. | 128/751 |
| 4,781,202 | 11/1988 | Janese | 128/754 |
| 4,790,315 | 12/1988 | Mueller, Jr. et al. | 128/344 |
| 4,793,350 | 12/1988 | Mar et al. | 128/344 |
| 4,793,351 | 12/1988 | Landman et al. | 128/344 |
| 4,815,478 | 3/1989 | Buchbinder et al. | 128/772 |
| 4,819,635 | 4/1989 | Shapiro | 128/752 |
| 4,832,048 | 5/1989 | Cohen | 128/786 |
| 4,844,087 | 7/1989 | Garg | 128/753 |
| 4,850,373 | 7/1989 | Zatloukal et al. | 128/749 |
| 4,867,156 | 9/1989 | Stack et al. | 128/305 |
| 4,873,991 | 10/1989 | Skinner | 128/754 |
| 4,877,030 | 10/1989 | Beck et al. | 128/343 |
| 4,877,031 | 10/1989 | Conway et al. | 128/344 |
| 4,877,037 | 10/1989 | Ko et al. | 128/756 |
| 4,887,613 | 12/1989 | Farr et al. | 606/159 |
| 4,903,709 | 2/1990 | Skinner | 128/754 |
| 4,925,450 | 5/1990 | Imonti et al. | 604/240 |
| 4,932,959 | 6/1990 | Horzewski | 606/194 |
| 4,953,559 | 9/1990 | Salerno | 128/751 |
| 4,961,430 | 10/1990 | Sheahon | 128/754 |
| 5,011,490 | 4/1991 | Fischell et al. | 604/22 |
| 5,135,483 | 8/1992 | Wagner et al. | 128/751 |

OTHER PUBLICATIONS

"Primary Pulmonary Hypertension: A Look at the Future" by John H. Newman, MD, Joseph C. Ross, MD, Sep. 1989, American College of Cardiology, pp. 551-555.

"Hypoxia-Induced Structural Changes in the Media and Adventitia of the Rat Hilar Pulmonary Artery and Their Regression", by Barbara Meyrick, PhD, and Lynne Reid, MD, Feb. 13, 1980, American Association of Pathologists, pp. 151-174.

(List continued on next page.)

Primary Examiner—Max Hindenburg
Attorney, Agent, or Firm—Stephen A. Gratton

[57] ABSTRACT

An arterial biopsy catheter for obtaining a biopsy sample from the inner layers of an artery includes an outer tube and an inner tube slidingly mounted within the outer tube. The inner tube is formed with a closed distal end having a beveled opening. The outer tube is formed with an open distal end having a sharpened circumferential edge adapted to cut arterial material in contact with the beveled opening by sliding the outer tube over the inner tube. The inner tube and outer tube are attached to handles for manipulation by an operator. In use, a vacuum is applied through the inside diameter of the inner tube to the beveled opening, to draw arterial material into contact with the beveled opening. The outer tube is then manipulated to sever the arterial material to form the biopsy sample. The inner and outer tubes are then withdrawn from the artery with the biopsy material held in the beveled opening.

18 Claims, 2 Drawing Sheets

OTHER PUBLICATIONS

"Pulmonary Hypertension: A Cellular Basis for Understanding the Pathophysiology and Treatment" by Stuart Rich, MD, FACC, Bruce H. Brundage MD, FACC, 1989, The American College of Cardiology, pp. 545–550.

"Proceedings of National Heart, Lung, and Blood Institute Pediatric Cardiology Workshop: Pulmonary Hypertension" by William F. Freidman, 1986, International Pediatric Research Foundation, Inc.

"The Prevalence of Pulmonary Hypertension in the United States", Stuart Rich, M.D., F.C.C.P., Eva Chomka, MD, Lawrence Hasara, MD, Kimberly Hart, RN, Terence Drizd, B.S., Esther Joo, MPH and Paul S. Levy, Sc.D. Oct. 17, 1988. pp. 236–241.

"Cardiac Diagnostic and Treatment" by Fowler 2nd Ed. Harper & Row, 1980.

"Cardiology: Fundamentals and Practice" by Robert O. Brandenburg, MD, Valentin Fuster, MD, Emilio R. Giuliani, MD, Dwight C. McGoon, MD. 1987.

"The Journal of Pediatrics" by Ronald M. Perkin, MD and Nick G. Anas, MD, Oct., 1984, pp. 511–515.

"Flexible Myocardial Biopsy Forceps" by William Cook, 1989.

"Put Our Diamonds in the Rough" *Introducing Rotablator*, 1990.

"Simpson Peripheral AtheroCath" Preparation and Proceudre. 1988.

"Simpson Peripheral AtheroCath" Design, 1989.

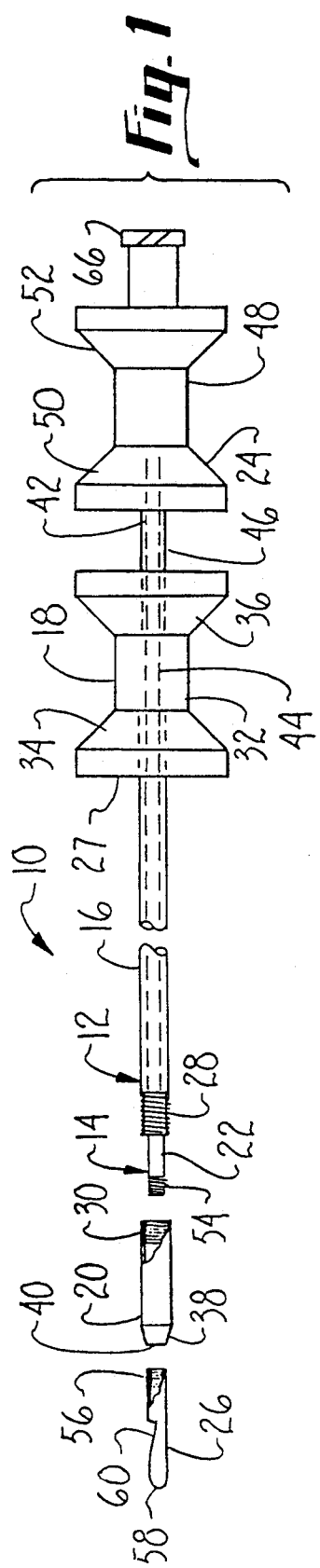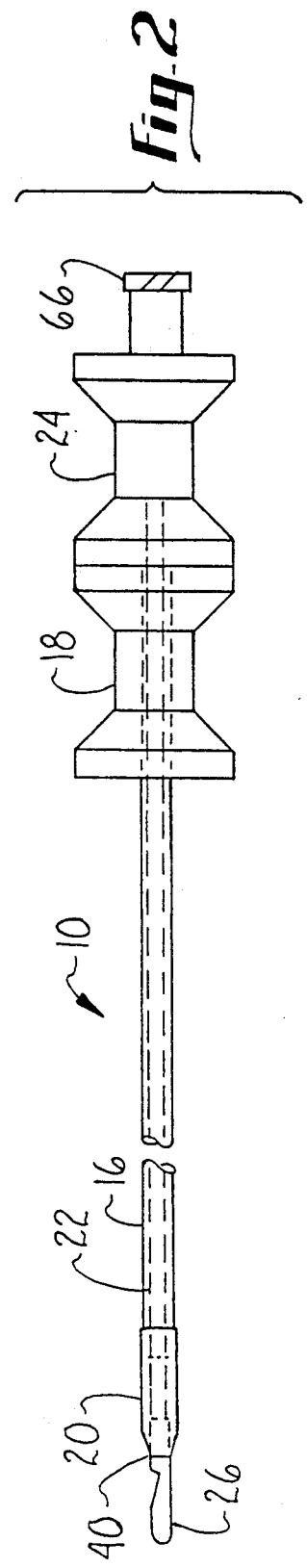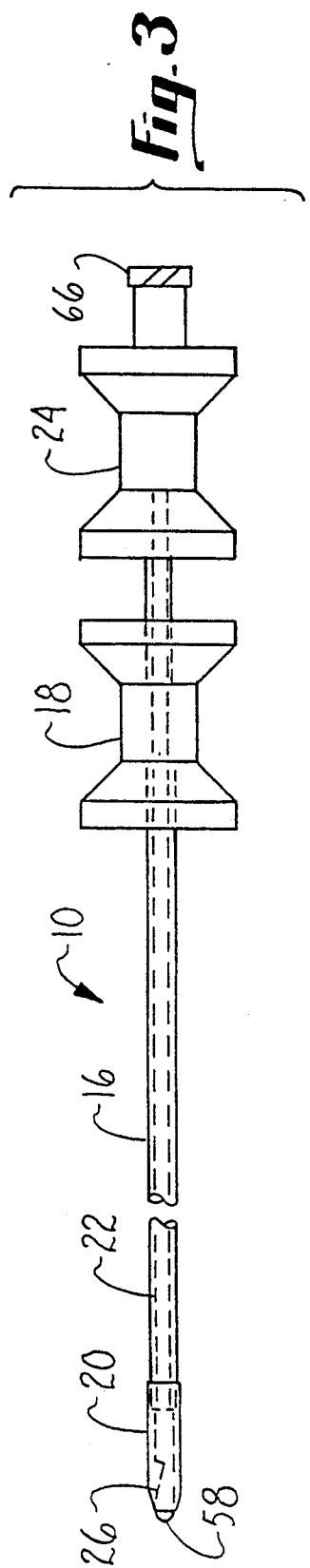

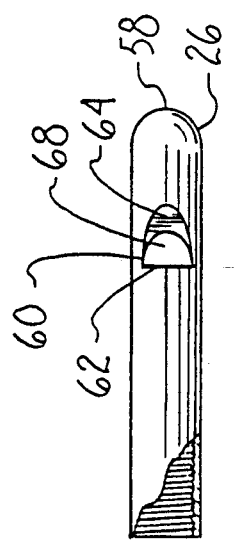
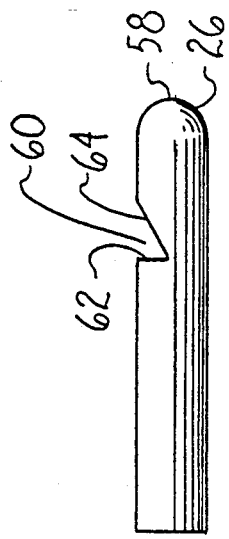
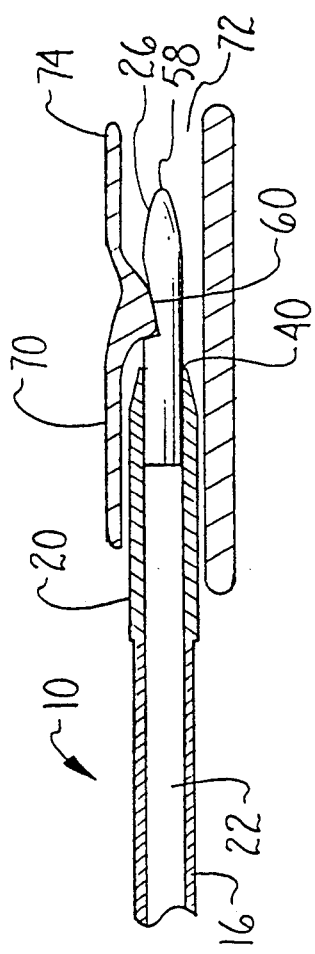
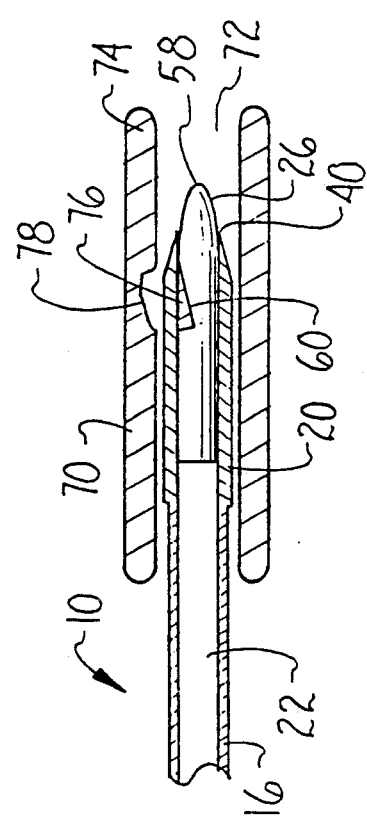

APPARATUS AND METHOD FOR OBTAINING AN ARTERIAL BIOPSY

TECHNICAL FIELD

This invention relates to medical instruments for extracting a biopsy specimen and more particularly to an apparatus and method for obtaining a biopsy from the inner layers of an arterial wall of a living being.

BACKGROUND OF THE INVENTION

Various cardiovascular catheters are well known in the art for performing different diagnostic and interventional medical procedures. In general most cardiovascular catheters include a slender flexible tube that is inserted into an artery of a patient and guided to an access site that allows the medical procedure to be performed.

As an example, an angioplasty catheter is used in a medical procedure in which an inflatable balloon is used to widen a stenotic segment of an artery. As another example, atherocatheters are used to perform another medical procedure known as atherectomy. This procedure cuts away the stenoses and then removes the pieces of plaque which comprised the stenosis from the artery using a vacuum source directed through the catheter.

Medical devices for obtaining a biopsy of different body structures such as the heart, muscles, intestines, and the uterus are also well known in the art. U.S. Pat. No. 3,606,878 to Kellogg, for instance, discloses an early instrument for extracting a biopsy specimen from different regions of the body such as the lungs, chest cavity liner, heart sac or other internal organs.

U.S. Patent No. 4,961,430 to Sheahon discloses a cervical biopsy instrument. U.S. Pat. Nos. 4,708,147 to Haaga, U.S. Pat. No. 4,640,296 to Schnepp-Pesch et al, and U.S. Pat. No. 4,620,547 to Boebel disclose particular needle structures for biopsy cannulas.

Other biopsy devices are disclosed in U.S. Pat. Nos. Nos. 4,850,373; 4,903,709; 4,953,559; 4,617,940; 4,099,518; and 4,873,991. Finally a medical instrument known in the art as a Schulz-Caves bioptome is an endomyocardial biopsy device for removing a biopsy sample from the heart.

In general, however, even though biopsy instruments are well known in the art there are no prior art biopsy instruments that are specifically adapted to obtaining a biopsy sample which comprises a segment of arterial wall. An arterial wall is a relatively thin structure. Consequently the possibility of a full-thickness puncture and a resultant hemorrhage exists.

Some of the above cited biopsy catheters, such as the Schulz-Caves bioptome, will remove a segment of tissue in a plane generally perpendicular to a longitudinal axis of the catheter. As is apparent, such an arrangement would be ineffective for use on a thin walled vessel or a long narrow artery. In addition some biopsy catheters are rigid and are not specifically designed for use in arteries.

Moreover, the tissue removed by some prior art biopsy catheters and atherocatheters in general, is not entirely suitable for a subsequent detailed biopsy examination because the tissue has been mutilated and subjected to multiple impacts by the application of a vacuum to the catheter. In addition, the orientation of the tissue in relation to the parent tissue may have been lost. Atherocatheters such as the Simpson Athero-Cath TM are designed to remove plaque from the artery and to avoid the arterial tissue.

Information gained from the study of such arterial tissue may be useful in determining the cause and treatment of various cardiovascular maladies. As an example, millions of people suffer from what is called essential hypertension. This hypertension is deemed essential because there is no known cause, let alone cure, for it. These people are treated by receiving drugs that reduce their blood volume or relax their vessels. These drugs do not cure their hypertension, nor shed any light on the underlying causes of high blood pressure.

The current technology allows a physician to take a blood pressure reading, do an angiogram (to visualize arterial profile) and take imperfect curative action if he can determine the cause of narrowing (i.e. fat deposits) and take palliative action if he cannot determine the cause.

The present invention is directed to an apparatus and method for advancing the current understanding of cardiovascular maladies such as hypertension. Another example of the usefulness of this catheter would be in the diagnosis and therapy of atherosclerosis. In this disease there is formation of lipid plaques in the arteries. Current therapies include dietary changes, lipid lowering drugs and interventional cardiology procedures such as balloon angioplasty, atherectomy, excimer laser treatment and stent implantation. However, all these treatment modalities are imperfect especially the interventional ones which have a high rate of early restenosis. The apparatus and method of the present application may be useful in obtaining tissue to determine the mechanism of disease and in evaluating the results of therapy including recently developed genetic techniques.

In addition the apparatus and method of the invention allows a more precise diagnosis of the underlying causes of a particular patient's condition. As an example the apparatus and method may also be helpful in studying differences between people suffering from a variety of vascular diseases. When a precise diagnosis is available, more accurate therapies can be prescribed and unnecessary treatments eliminated.

Accordingly it is an object of the present invention to provide an apparatus and method for obtaining a biopsy sample from the inner layers of a blood vessel such as an artery of a living person. It is another object of the present invention to provide an apparatus and method for obtaining a biopsy sample from the inner layers of a vessel such as an artery in which the biopsy sample is retrieved while minimizing the impacts the biopsy sample would be subject to as would occur with the use of atherocatheters and prior art biopsy catheters that utilize vacuum aspiration to retrieve a sample. It is a further object of the present invention to provide an apparatus and method for obtaining a biopsy sample from a vessel wall in which the orientation of the biopsy sample relative to the parent tissue is preserved. It is yet another object of the present invention to provide an apparatus for obtaining a biopsy sample from an artery of a living person that is relatively easy to use by medical personnel and in which the risk of damage to or puncture of the arterial wall is minimized. It is a further object of the present invention to provide an apparatus for obtaining a biopsy sample from an arterial wall that is simple in construction and relatively inexpensive to manufacture.

SUMMARY OF THE INVENTION

In accordance with the present invention an apparatus and method for obtaining a biopsy sample from an arterial wall or body part of a living being is provided. The apparatus of the invention is a biopsy catheter adapted for use with a vacuum source to mechanically cut a sample of tissue from the arterial wall without puncturing the artery and then to remove the sample from the artery with little or no damage to the sample. The biopsy catheter includes an inner tube slidably disposed within an outer tube. Handles are attached to both the inner tube and the outer tube for manipulating the tubes within the artery and for manipulating the outer tube with respect to the inner tube.

The inner tube includes a closed tip portion at a distal end having a beveled hole for contacting the arterial wall upon application of a vacuum through the inner tube. The outer tube is open at a distal end and is formed with a sharpened edge adapted to slide over the inner tube and cut the arterial material held in the beveled hole of the inner tube by the vacuum. A sample thus cut is held in the beveled hole by the vacuum and can be removed by withdrawal of the biopsy catheter from the artery.

The novel features of this invention, as well as the invention itself, both as to its structure and its operation, will be best understood from the accompanying drawings, taken in conjunction with the accompanying description, in which similar reference characters refer to similar parts.

BRIEF DESCRIPTION OF THE DRAWINGS

FIG. 1 is an exploded side elevation view of a biopsy catheter constructed in accordance with the present invention;

FIG. 2 is a side elevation view of a biopsy catheter constructed in accordance with the present invention shown with the distal tip of an inner tube exposed to cut a biopsy sample from the artery;

FIG. 3 is a side elevation view of a biopsy catheter constructed in accordance with the present invention shown with the distal tip of the inner tube retracted into an outer tube;

FIG. 4 is a schematic view of a distal portion of the catheter located within an artery and shown with a beveled opening of the inner tube contacting a sidewall of the artery;

FIG. 5 is a schematic view of the distal portion of the catheter located within an artery and shown with a portion of the artery cut by a sharpened edge of the outer tube and held within the beveled opening of the inner tube;

FIG. 6 is an enlarged view of the distal portion of the inner tube showing the beveled opening formed in the inner tube; and FIG. 7 is a side elevation view of FIG. 6.

DESCRIPTION OF PREFERRED EMBODIMENTS

Referring now to FIGURE a biopsy catheter constructed in accordance with the invention is shown and generally designated as 10. The biopsy catheter 10 comprises an outer tube assembly 12 and an inner tube assembly 14. The outer tube assembly 12 includes an outer tube 16, an outer tube handle 18, and a cutter tip 20. The inner tube assembly 14 includes an inner tube 22, an inner tube handle 24, and suction tip 26.

The outer tube 16 is formed of a length of flexible tubing of a polymeric material such as polyterafluroethylene, nylon, or polyurethane. The outer tube 16 is sized with an outside diameter that will pass freely through an artery of a human being and with a length that will allow access to an arterial site within the body. In addition, the outer tube 16 must be flexible enough to bend through the tortuous path of an artery yet rigid enough to transmit compressive and tensile forces linearly from the outer tube handle 18 to the cutter tip 20.

A proximal end 27 of the outer tube 16 is connected to the outer tube handle 18 using an attachment means such as an adhesive. Alternately this connection may be made using mating threads or fasteners. The outer tube handle 18 is formed of a rigid material such as hard plastic and is sized and shaped for manipulation by an operator's thumb and index finger. As such, the outer tube handle 18 is formed with a generally cylindrically shaped mid portion 32 and generally conically shaped end portions 34, 36.

A distal end of the outer tube 16 is threaded with an external thread 28. The cutter tip 20 of the outer tube assembly 12 is formed with a mating internal thread 30 for connecting the cutter tip 20 to the outer tube 16. Alternately (or in conjunction) other fastening means such as an adhesive may be utilized to connect the cutter tip 20 to the outer tube 16.

The cutter tip 20 is generally cylindrical in shape and has open ends. The cutter tip 20 is formed with a tapered distal portion 38 that terminates in a sharpened circumferential edge 40. The outside diameter of the cutter tip 20 is sized to enable passage through an artery. In general, the cutter tip 20 has the largest diameter of the portion of the biopsy catheter 10 that's in the body. The dimensioning of the outside diameter of the cutter tip 20 is thus critical in sizing a catheter 10 for a particular patient. As an example different sized catheters may be used for pediatric, adolescent and adult patients.

The inside diameter of the cutter tip 20 is sized slightly larger (i.e. .001) than the outside diameter of the suction tip 26 of the inner tube 22. The cutter tip 20 can thus be slid over the suction tip 26 by manipulation of the outer tube handle 18 allowing the sharpened circumferential edge 40 of the cutter tip 20 to cut a tissue sample held in the suction tip 26. The cutter tip 20 is preferably formed of a relatively hard material such as stainless steel.

The inner tube 22 is slidably mounted within the outer tube 16 and may be formed of a flexible polymeric material such as teflon, nylon, or polyurethane. As with the outer tube 16 the inner tube 22 must be flexible enough to allow passage through the tortuous path of an artery but rigid enough to transmit compressive and tensile forces linearly from the inner tube handle 24 to the suction tip 26. Alternately, the inner tube 22 and outer tube 16 may be formed of different polymeric materials suitable to their particular function (i.e. outer tube—polyterafluroethylene, inner tube—polyurethane).

A proximal end 42 of the inner tube 2 is connected to the inner tube handle 24 using an attachment means such as an adhesive. Alternately (or in conjunction) other fastening means such as mating threads or fasteners may be utilized to connect the inner tube 22 to the inner tube handle 24. The inner tube 22 passes through an opening 44 formed in the outer tube handle 18.

The inner tube 22 is reinforced with a larger diameter reinforcing tube 46 adjacent to its proximal end 42. The outer tube handle 18 is slidable over this larger diameter reinforcing tube 46. The inner tube handle 24 is identical in construction to the outer tube handle 18 and includes a cylindrical middle portion 48 and generally conically shaped end portions 50, 52. The inner tube handle 24 is adapted to be manipulated between the thumb and index finger of an operator to navigate the outer tube 16 through an artery and to slide the inner tube 22 with respect to the outer tube 16. A tube fitting 66 is connected to a proximal end of the inner tube handle 24 in fluid communication with an inside diameter of the inner tube 22 for connection to a vacuum source (not shown). This allows a vacuum to be directed through the inside diameter of the inner tube 22 and to the suction tip 26 of the inner tube 22. The vacuum being directed through the inner tube assembly of the catheter from tube fitting 66 to suction tip 26.

A distal end of the inner tube 22 is threaded with an external thread 54. The suction tip 26 of the inner tube assembly 14 is formed with a mating internal thread 56 at its proximal end for connecting the suction tip 26 to the inner tube 22. Alternately (or in conjunction) other fastening means such as an adhesive may be utilized to connect the suction tip 26 to the inner tube 22. The distal end 58 of the suction tip 26 is closed and air tight (i.e. hermetically closed) and formed with a rounded or hemispherically shaped surface.

With reference to FIGS. 6 and 7 a beveled opening 60 is formed in the suction tip 26 for holding a tissue sample from the artery. The beveled opening 60 is located along an outer circumferential surface of the suction tip and is in fluid communication with the inside diameter of the inner tube 22. As shown in FIG. 7 the beveled opening 60 is formed by the intersection of an end surface 62 situated generally perpendicular to a longitudinal axis of the suction tip 26 and a beveled surface 64 situated at an angle to a longitudinal axis of the suction tip 26. This forms an aperture 68 to the inside diameter of the inner tube 22. The depth of the end surface 62 is determined by the thickness of the wall of the suction tip 26 and by the angle of the beveled surface 64. This depth ultimately determines the thickness of the tissue sample and the depth of a cut into the artery.

With this arrangement an area of the artery contacted by an outer periphery of the beveled opening 60 is larger than the size of the aperture 68 to the inside diameter of the suction tip 26. A tissue sample can thus be held in the beveled opening 60 by a vacuum directed through the inside diameter of the inner tube 22 but will not pass through the aperture 68 to the inside diameter of the inner tube 22.

Referring now to FIG. 2 and 3 the biopsy catheter 10 is shown with the suction tip 26 in two different positions. As shown in FIG. 2 the suction tip 26 of the inner tube 22 can be extended outside of the cutter tip 20. In its extended position the suction tip 26 is situated for contacting the arterial wall. In the extended position of the suction tip 26 the outer tube handle 18 is in contact with the inner tube handle 24.

As shown in FIG. 3 the outer tube handle 18 can be pushed outward with respect to the inner tube handle 24 by the operator. This pushes the cutter tip 20 over the suction tip 26 and covers the suction tip 26 for insertion into and retraction from the artery.

OPERATION

Referring now to FIGS. 4 and 5 the arterial biopsy catheter 10 is shown in use for retrieving a biopsy sample from the inner layers of an artery 70. The artery 70 includes a lumen 72 and a sidewall 74. The biopsy catheter must be sterilized before it comes in contact with the patient, and it is intended for use in a sterile area such as an operating room. The biopsy catheter 10 is placed into the lumen 72 of the artery 70 utilizing an introducer catheter (not shown). The introducer catheter can be steered through the artery 70 and located at an arterial site to be sampled using techniques that are known in the art.

During insertion into the artery 70, the outer tube handle 18 and inner tube handle 24 are separated so that the suction tip 26 is retracted into the cutter tip 20 substantially as shown in FIG. 3. In this position only the rounded tip 58 of the suction tip 26 is exposed. The rounded tip 58 of the suction tip 26 of the biopsy catheter 10 is then steered through the introducer catheter to the arterial site where a tissue sample is to be obtained.

The biopsy catheter 10 may be steered through the artery 70 within the introducer catheter by manipulation of the outer tube 16 and the handles 18, 24 that remain outside of the patients body. No vacuum is applied to the inner tube 22 during insertion of the biopsy catheter 10 into the artery 70.

Once the distal tip 58 of the biopsy catheter 10 reaches the distal end of the introducer catheter the biopsy catheter 10 is located in the area of the artery 70 where the biopsy sample is to be obtained. The outer tube handle 18 is then pulled back by the operator until it comes into contact with the inner tube handle 24. This causes the cutter tip 20 to slide back from the suction tip 58 and exposes the beveled opening 60 in the suction tip 26.

When the suction tip 26 is exposed to the inner layers of the arterial wall 74 a vacuum source (not shown) is connected to the vacuum tube connection 66 (FIG. 1) of the inner tube 22. A disposable vacuum canister (not shown) is located between the tube connection 66 and vacuum source for collecting solid and liquid refuse.

The vacuum is then turned on, and after a small amount of blood is aspirated into the vacuum canister, the arterial wall 74 is pulled into the beveled opening 60 formed in the suction tip 26. The outer tube handle 18 is then pushed away from the inner tube handle 24 by the operator. This motion is transmitted by the outer tube 16 to the cutter tip 20 which slides over the suction tip 26. As the cutter tip 20 moves over the suction tip 26 the sharpened circumferential edge 40 of the cutter tip 20 severs a tissue sample 76 from the artery wall 74 leaving a void 78 in the wall 74. The suction provided by the vacuum source holds the tissue sample 76 against the beveled opening 60 during this cutting motion.

The tissue sample 76 severed is sized and shaped by the outer peripheral edge 69 of the beveled opening 60. Since the outer peripheral edge 69 of the beveled opening 60 is larger than the aperture 68 (FIG. 6) of the beveled opening 60 to the inside diameter of the inner tube 22, the tissue sample 76 severed is also larger than this aperture 68. The tissue sample 76 thus will not pass through the aperture 68. This is important because if the biopsy sample 76 were suctioned into the inside diameter of the inner tube 22 much structural and possibly cellular information may be lost. In addition the orientation of the tissue sample 76 with respect to the arterial wall 74 is preserved. The size and depth of the beveled hole 60 are carefully constrained to minimize the risk of breaching the arterial wall 74 and subsequent hemorrhage.

After the tissue sample 76 has been cut, the vacuum is turned off, and the outer tube 16 of the biopsy catheter 10 is pulled from the artery 70 with the inner suction tip 58 covered by the cutter tip 20. The tissue sample 76 is held in place in the suction tip 26 and protected during withdrawal by the cutter tip 20.

Once the catheter 10 is fully outside the patient, the outer handle 18 is pulled back toward the inner handle 24, exposing the suction tip 26 which contains the tissue sample 76 of the inner layers of the patient's artery 70. This tissue sample 76 can be analyzed and used to ascertain the patient's vascular diseases. The tissue sample 76 can be examined macroscopically, microscopically or by the newest techniques of cellular and molecular biology.

After the biopsy sample has been removed, the biopsy catheter 10 can be reintroduced to take another sample if desired or necessary. This biopsy can be from the same area of the patient's vasculature, or another area can be reached by repositioning the introducer catheter. After the biopsy procedure is complete the biopsy catheter 10 is disposed.

Thus, the invention provides a simple yet unobvious method and apparatus for obtaining a biopsy sample from the inner layers of an arterial wall. While the method of the invention has been described with reference to a preferred embodiment thereof, for obtaining a biopsy sample from the wall of an artery it is understood that the inventive concepts discussed herein can be used to obtain a biopsy sample from a body portion of a living being other than an artery. As an example, such a catheter could be used to obtain a biopsy sample from the abdomen, intestine, colon, esophagus or other body part. As will be apparent to those skilled in the art, therefore certain changes and modifications can be made without departing from the scope of the invention as defined by the following claims.

I claim:

1. A catheter for insertion into an artery for obtaining a tissue sample from an arterial wall of a living being comprising:
    a substantially flexible outer tube formed with an open distal end having a sharpened edge;
    a substantially flexible inner tube slidably mounted within the outer tube and having a closed distal end and an opening formed to an inside diameter thereof;
    means for applying a vacuum through the opening in the distal end of the inner tube for drawing tissue into contact with the opening; and
    means for moving the sharpened edge of the outer tube over the opening in the inner tube to cut a tissue sample with the tissue sample retained within the opening and protected by the outer tube for withdrawing the tissue sample from the artery.

2. A catheter as claimed in claim 1 and wherein the opening in the inner tube has a beveled exterior surface to form an area for contact with the tissue that is larger than an aperture of the opening to the inside diameter of the inner tube.

3. A catheter as claimed in claim 2 and wherein the means for moving the sharpened edge of the outer tube over the opening in the inner tube includes a handle attached to the outer tube.

4. A catheter as claimed in claim 3 and wherein the means for moving the sharpened edge of the outer tube over the opening in the inner tube includes a handle attached to the inner tube.

5. A catheter as claimed in claim 2 and wherein the means for applying a vacuum includes a tube fitting in fluid communication with an inside diameter of the inner tube.

6. A catheter for insertion into an artery of a living being for obtaining a biopsy sample from an inner layer of an arterial wall, comprising:
    a substantially flexible inner tube having a suction tip formed at a closed distal end and including an opening in fluid communication with an inside diameter of the inner tube with the opening formed with an outer periphery on an outer surface of the inner tube and with the opening larger than an aperture to the inside diameter thereof;
    a substantially flexible outer tube slidably mounted over the inner tube and formed with a cutter tip at an open distal end sized to slide over the inner tube and cut tissue in contact with the opening in the inner tube;
    an inner tube handle attached to the inner tube and an outer tube handle attached to the outer tube for manipulating the catheter and the inner and outer tubes relative to one another; and
    means for applying a vacuum to the inside diameter of the inner tube and through the opening to draw tissue into contact with the opening for cutting by the cutter tip with the tissue sample retained in the opening and protected by the outer tube for withdrawing the tissue sample from the artery.

7. A catheter as claimed in claim 6 and wherein the opening is formed with a beveled exterior surface.

8. A catheter as claimed in claim 7 and wherein the open end of the cutter tip is formed with a sharpened circumferential edge.

9. A catheter as claimed in claim 8 and wherein the cutter tip is formed of metal.

10. A catheter as claimed in claim 9 and wherein the outer tube is formed of a polymeric material.

11. A catheter as claimed in claim 10 and wherein the suction tip is formed of metal.

12. A catheter as claimed in claim 11 and wherein the inner tube is formed of a polymeric material.

13. A catheter as claimed in claim 12 and wherein the inner tube is reinforced with a larger diameter tubing at a distal end and the outer tube handle slides over the larger diameter tubing.

14. A method of obtaining a biopsy sample from an inner layer of an arterial wall of an artery of a living being comprising:
    inserting a catheter into the artery having an inner tube formed with an opening and a closed distal end slidingly mounted to an outer tube formed with an open distal end;
    positioning the opening of the inner tube outside of a distal end of the outer tube;
    applying a vacuum to the inner tube to draw and retain arterial wall tissue into the opening formed in the inner tube;
    sliding the outer tube over the inner tube to cut and protect the tissue retained in the opening; and
    removing the inner tube and outer tube from the artery with the biopsy sample retained in the opening and protected by the outer tube.

15. A method of obtaining a biopsy sample as claimed in claim 14 and wherein the method is used to determine the causes of arterial wall disease.

16. A method of obtaining a biopsy sample as claimed in claim 14 wherein the opening is formed with a beveled outer surface.

17. A method of obtaining a biopsy sample as claimed in claim 16 and wherein the outer tube is formed with a sharpened circumferential edge on an open distal end.

18. A method for obtaining a biopsy sample from an artery of a living being comprising:
   a) inserting a catheter into the artery said catheter including:
      a substantially flexible outer tube formed with an open distal end having a sharpened edge;
      a substantially flexible inner tube slidably mounted within the outer tube and having a closed distal end and an opening formed to an inside diameter thereof;
      means for applying a vacuum through the opening in the distal end of the inner tube for drawing tissue of the arterial wall into contact with the opening; and
      means for moving the sharpened edge of the outer tube over the opening in the inner tube to cut and retain a tissue sample from the arterial wall;
   b) contacting the arterial wall with the catheter;
   c) cutting a biopsy sample from the arterial wall;
   d) retaining the biopsy sample within the opening formed in the catheter; and
   e) withdrawing the catheter with the retained biopsy sample.

* * * * *

UNITED STATES PATENT AND TRADEMARK OFFICE
CERTIFICATE OF CORRECTION

PATENT NO. : 5,287,857
DATED     : February 22, 1994
INVENTOR(S) : David Mann

It is certified that error appears in the above-indentified patent and that said Letters Patent is hereby corrected as shown below:

Col 3, line 61
    after Figure, add --1--.

Signed and Sealed this

Tenth Day of October, 1995

*Attest:*

BRUCE LEHMAN

*Attesting Officer*    *Commissioner of Patents and Trademarks*